United States Patent Office

Plant Pat. 2,142
Patented Apr. 24, 1962

2,142
ROSE PLANT

Marie Louise Meilland (nee Paolino), Cap d'Antibes, Alpes Maritimes, France, assignor to The Conard-Pyle Company, West Grove, Pa., a corporation of Pennsylvania Filed May 2, 1961, Ser. No. 107,274
1 Claim. (Cl. 47—61)

The present invention relates to a new and distinct variety of rose plant of the hybrid tea class, which was originated by me by crossing the variety "Radar" (unpatented) with the variety "Caprice" (unpatented).

The primary objective of this breeding was to produce a new rose variety in which there is combined the vigorous and bushy habit of growth of the parent variety "Caprice," with the non-Bluing Red general flower coloration of the parent variety "Radar." This objective was fully achieved, along with other desirable improvements, as evidenced by the following unique combination of characteristics which are outstanding in the new variety and which distinguish it from its parents, as well as from all other varieties of which I am aware:

(1) A bushy, well branched, and quite strong habit of growth, but of somewhat less than average height, thereby making this variety of particular value for garden decoration;

(2) Attractive and distinctive foliage which changes in color from Maroon to Parsley Green as the foliage matures;

(3) A profuse blooming habit;

(4) Excellent flower form; and (5) A distinctive multi-toned general color tonality of the flowers varying in the open flower from Rose Red through Phlox Pink to Primrose Yellow at the base of the petals.

Asexual reproduction of the new variety by budding, as performed at West Grove, Pennsylvania, U.S.A., and also in France, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obvious:

Type: Hardy; bush; outdoor; seedling; for garden decoration.
Class: Hybrid tea.
Breeding: Seedling.
*Seed parent.*—"Radar."
*Pollen parent.*—"Caprice."
Propagation: Holds its distinguishing characteristics through succeeding propagations by budding.

*Flower*

Locality where grown and observed: West Grove, Pennsylvania, U.S.A.
Flowers borne: Sometimes singly and sometimes from 3 to 5 per stem; in regular flat cluster; on stems of normal strength and from short to medium length.
Quantity of bloom: Abundant, outdoors.
Continuity: Continuous.
Fragrance: Slight. Nature—tea.
Bud:
*Peduncle.*—From short to medium length; medium caliper; erect; almost smooth; with few hairs of Lettuce Green color, Plate 861/1 having points of Oxblood Red, Plate 00823/3. Color—Lettuce Green, Plate 861/1.
*Before calyx breaks.* — Size — medium. Form—medium length; ovoid; with a conspicuous neck; with foliaceous appendages on the surface of the bud; with bristle-like foliaceous parts extending beyond the tip of the bud equal to ¼ of its length.
*As calyx breaks.*—Color—Chrysanthemum Crimson, Plate 824/1.
*As first petal opens.* — Size — medium. Form—medium length; pointed. Color: outside—Cherry, Plate 722/3, grading to Rose Madder, Plate 23/1, then to Dawn Pink, Plate 523/2 at base, with point of attachment Primrose Yellow, Plate 601/1; inside—slightly darker than Rose Red, Plate 724, grading to Spiraea Red, Plate 025, and then to Fuchsine Pink, Plate 627/3, with base Primrose Yellow, Plate 601/1.
*Opening.*—Opens up well.
Bloom:
*Size (when fully open).*—Medium; from 3½ inches to 3¾ inches.
*Petalage.*—Double; from 25 to 35 petals; arranged regularly.
*Form.*—High-centered at first but becoming cupped; petals being at first very loosely rolled outward but later becoming flat at maturity.
Petals: Medium thickness; with inside velvety and outside satiny. Shape: outer—obovate, scalloped; intermediate—obovate, scalloped; inner—obovate, irregular.

This description of a newly opened flower was made from a rose grown outdoors during the month of September at West Grove, Pennsylvania, U.S.A.:

*Color.*—Outer petal: outside surface—Tyrian Rose, Plate 24/2, shaded with Tyrian Rose, Plate 24/1 where first exposed to sun, with base of petal and point of attachment Dresden Yellow, Plate 64/3; inside surface—slightly darker than Rose Red, Plate 724 over upper half of petal, grading to Phlox Pink, Plate 625/1 and then to Phlox Pink, Plate 625/3, with point of attachment Primose Yellow, Plate 601/1. Intermediate petal: outside surface—Tyrian Rose, Plate 24/2, with base of petal and point of attachment Dresden Yellow, Plate 64/3; inside surface—Rose Red, Plate 724/2 in the form of a wide border, grading to Phlox Pink, Plate 625/1 and then to Phlox Pink, Plate 625/3 at base of petal, with point of attachment Primrose Yellow, Plate 601/1. Inner petal: outside surface—Tyrian Rose, Plate 24/2, grading to Tyrian Rose, Plate 24/3 at base, with point of attachment Dresden Yellow, Plate 64/3; inside surface—Rose Red, Plate 724/1, grading to Phlox Pink, Plate 625/1 and then to Phlox Pink, Plate 625/3 at base, with point of attachment Primrose Yellow, Plate 601/1.

This description was made from a rose that was open for 3 days outdoors during the month of September at West Grove, Pennsylvania, U.S.A.:

*Color.*—Outer petal: outside surface—Tyrian Rose, Plate 24/2, with base of petal and point of attachment Dresden Yellow, Plate 64/3; inside surface—slightly darker than Rose Red, Plate 724 over upper half of petal, grading to Rose Red, Plate 724/2 and then to Phlox Pink, Plate 625/3 over basal quarter of petal, with point of attachment Primrose Yellow, Plate 601/3. Inner petal: outside surface—Tyrian Rose, Plate 24/2, with base of petal and point of attachment Dresden Yellow, Plate 64/3; inside surface—upper margin of petal Rose Red, Plate 724, grading to Phlox Pink, Plate 625/1 and then to Phlox Pink, Plate 625/3, with base of petal Primrose Yellow, Plate 601/3.

*General color effect.*—Newly opened flower—Rose Red, Plate 724, grading to Phlox Pink, Plate 625/1, with reverse of petals showing Tyrian Rose, Plate 24/2. 3-days open—Rose Red, Plate 724 at margin of petal, grading to Phlox Pink, Plate 625/1, with reverse of petals showing Tyrian Rose, Plate 24/2.

*Behavior.*—Drop off cleanly.

*Flower longevity.*—On bush in garden—4 days in September. Cut roses grown outdoors and kept at living room temperatures—5 days in September.

*Reproductive Organs*

Stamens: Medium number; arranged regularly about pistils.

Filaments: Most with anthers. Color—Mandarin Red, Plate 17/3.

Anthers: Small; all open at once; occasionally an anther fused with a petaloid. Color—Buttercup Yellow, Plate 5/1.

Pollen: Sparse. Color—Buttercup Yellow, Plate 5/1.

Pistils: Medium number.

Styles: Uneven; medium length; thin; bunched.

Stigma: Color—Straw Yellow, Plate 604/2.

Ovaries: All enclosed in receptacle.

Hips: None observed.

Sepals: Permanent; moderately long; spear-shaped.

Seeds: None observed.

*Plant*

Foliage:

*Leaves.*—Compound of 3, 5 or 7 leaflets; normal abundance; medium size; leathery.

*Leaflets.*—Shape—oval, with apex acute. Base—obtuse. Margin—simply serrate.

*Color.*—Mature: upper surface—Parsley Green, Plate 00962, thinly margined with Maroon, Plate 1030; under side—Willow Green, Plate 000862/1, lightly overlaid with Erythrite Red intermediate between 0027/2 and 0027/3. Young: upper side—Parsley Green, Plate 00962, heavily overlaid with Maroon, Plate 1030; under side—Willow Green, Plate 000862/1, overlaid with between Erythrite Red, Plate 0027/2 and Erythrite Red, Plate 0027/3.

*Rachis (the supporting stem of the compound leaf).*—Medium caliper. Upper side—grooved; hairy. Under side—sparsley prickly.

*Stipules.*—Medium length; moderately narrow; with points of medium length turning out at an angle of about 45°.

*Disease resistance.*—Comparable to that of the average variety grown under the same cultural conditions at West Grove, Pennsylvania, U.S.A.

Growth:

*Habit.*—Bushy; much-branched.

*Growth.*—Vigorous.

*Canes.*—Medium caliper.

*Main stems.*—Dull. Color —Spinach Green, Plate 0960/2. Prickles—several; color—Garnet Brown, Plate 00918/1. Hairs—none.

*Branches.*—Dull. Color—Spinach Green, Plate 0960/2. Prickles—several; color—Sap Green, Plate 0862/3. Hairs—none.

*New shoots.*—Dull. Color—near Maroon, Plate 1030/3. Prickles—several; color—slightly darker than Erythrite Red, Plate 0027. Hairs—none.

I claim:

A new and distinct variety or rose plant of the hybrid tea class, substantially as herein shown and described, characterized particularly as to novelty by the unique combination of a bushy, well-branched and quite strong habit of growth, but somewhat below average height, attractive and distinctive foliage which changes in color from Maroon to Parsley Green as the foliage matures, a profuse blooming habit, excellent flower form, and a distinctive multi-toned general color tonality of the flowers varying in the open flower from Rose Red through Phlox Pink to Primrose Yellow at the base of the petals.

No references cited.

April 24, 1962 MARIE LOUISE MEILLAND (NEE PAOLINO) ROSE PLANT Filed May 2, 1961 Plant Pat. 2,142
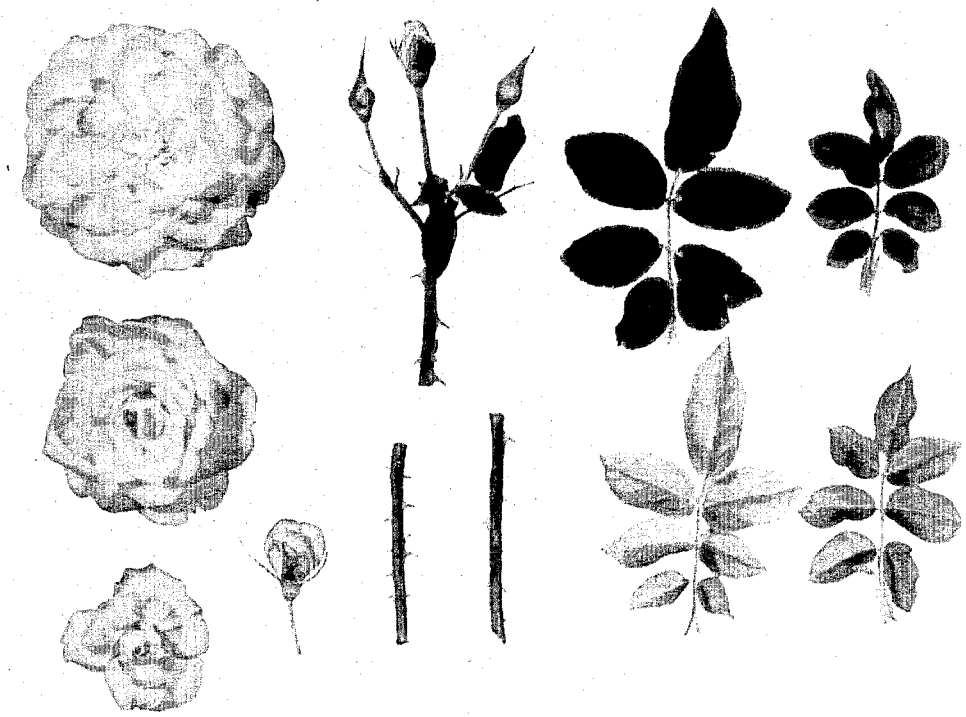
Inventor.
Marie Louise Meilland
(Née Paolino)
By: Robb & Robb
Attorneys.